(12) United States Patent
Padgett

(10) Patent No.: US 8,709,714 B2
(45) Date of Patent: Apr. 29, 2014

(54) LAMINAR LIBRARY SCREEN

(71) Applicant: Hal S. Padgett, Vacaville, CA (US)

(72) Inventor: Hal S. Padgett, Vacaville, CA (US)

( * ) Notice: Subject to any disclaimer, the term of this patent is extended or adjusted under 35 U.S.C. 154(b) by 0 days.

(21) Appl. No.: 13/752,376

(22) Filed: Jan. 28, 2013

(65) Prior Publication Data

US 2013/0137600 A1    May 30, 2013

Related U.S. Application Data

(62) Division of application No. 12/972,067, filed on Dec. 17, 2010, now Pat. No. 8,383,334.

(60) Provisional application No. 61/288,138, filed on Dec. 18, 2009.

(51) Int. Cl.
  *C12Q 1/70*    (2006.01)
  *C12Q 1/00*    (2006.01)
  *C12Q 1/68*    (2006.01)
  *G01N 33/53*   (2006.01)

(52) U.S. Cl.
  USPC ...................... 435/5; 435/4; 435/6.1; 435/7.1

(58) Field of Classification Search
  None
  See application file for complete search history.

(56) References Cited

U.S. PATENT DOCUMENTS 6,468,745 B1 * 10/2002 Fitzmaurice et al. ........ 435/6.16

OTHER PUBLICATIONS

Kurien and Scofield. Western blotting. Methods, vol. 38, pp. 283-293, 2006.*
Moneoliva and Albar. Differential proteomics: An overview of gel and non-gel based approaches. Briefings in Functional Genomics and Proteomics, vol. 3, No. 3, pp. 220-239, Nov. 2004.*
Daoust, A., "Localization of Deoxyribonuclease in Tissue Sections", Experimental Cell Research 12 (1957) 203-211.
Varner, J.E. and Ye, Z. "Tissue Printing", FASEB J 8 (1994) 378-384.

* cited by examiner

*Primary Examiner* — Jennifer Dunston
(74) *Attorney, Agent, or Firm* — Wayne P. Fitzmaurice

(57) ABSTRACT

Described is a method of screening libraries of variant proteins produced in plant leaves using a plant viral vector to identify a gene of interest comprising, inoculating leaves with a library of viruses expressing variant genes, allowing time for infected foci to form, harvesting a leaf, sticking one face of the leaf to a sticky support material to immobilize the leaf and leaving the opposing face of the leaf exposed, abrading the exposed face with granular material, placing the abraded face in contact with a blot membrane having a backing comprising blotting paper, placing the assembly into a vacuum seal bag; evacuating and sealing the bag; removing the assembly and separating the membrane, performing an assay on the membrane to identify an infected focus of interest; recovering virus corresponding to the infected focus; recovering nucleic acid from the virus, and identifying the gene of interest from the nucleic acid.

5 Claims, 5 Drawing Sheets

LAMINAR LIBRARY SCREEN

CROSS REFERENCE TO RELATED APPLICATIONS

This application is a Divisional application of U.S. application Ser. No. 12/972,067 (now U.S. Pat. No. 8,383,334) filed Dec. 17, 2010 that claims priority from U.S. Provisional application Ser. No. 61/288,138, filed Dec. 18, 2009.

BACKGROUND OF THE INVENTION

A number of efficient methods have been developed for producing large libraries of variant genes and for expressing and screening those genes in a rapid and cost effective manner. A key element of any gene library-screening program is to maintain an association between gene and protein, so that when desirable variant proteins are identified, the genes encoding them can be recovered. One approach to maintaining the gene-protein correspondence is to distribute the clones into orderly arrays that can then be archived and replicated for expression and screening studies. While this is a straightforward and effective method for maintaining gene-protein correspondence, it is laborious and expensive to implement, especially with large libraries. Other approaches for manipulating and screening large gene-protein libraries involve display on the surface of virus particles or cells. These methods permit mass screening of many thousands to millions of variants. Most applications of display technologies have been based on prokaryotic systems and therefore do not provide for expression of proteins that may require expression in a eukaryotic host.

What is needed in the art is a eukaryotic expression system that supports expression of large libraries in a eukaryotic host while maintaining a correspondence between gene and protein. In conjunction, it may also be useful to employ an expression system that can produce larger amounts of protein than can be produced in a single cell.

BRIEF SUMMARY OF THE INVENTION

One aspect of the present invention comprises a method of screening libraries of variant proteins produced in plant leaves using a plant viral vector to identify a gene of interest, the method comprising: a) inoculating plant leaves with a library of viruses expressing variant genes; b) allowing sufficient time for a plurality of infected foci to form; c) harvesting a leaf with infected foci, the leaf having two opposing faces; d) sticking one face of the leaf to a sticky support material to immobilize the leaf and leaving the opposing face of the leaf exposed to form an exposed face; e) abrading the exposed face of the leaf with granular material to form an abraded face; f) placing the abraded face in contact with a blot membrane having a backing comprising blotting paper to form an assembly; g) placing the assembly into a vacuum seal bag; h) removing air and sealing the vacuum seal bag; i) removing the assembly and separating the blot membrane from the assembly; j) performing an assay on the separated blot membrane to identify an infected focus of interest; k) recovering virus of interest corresponding to the infected focus of interest; l) recovering nucleic acid from the virus of interest; and m) identifying the gene of interest from the nucleic acid.

DETAILED DESCRIPTION OF THE INVENTION

Figure 1:
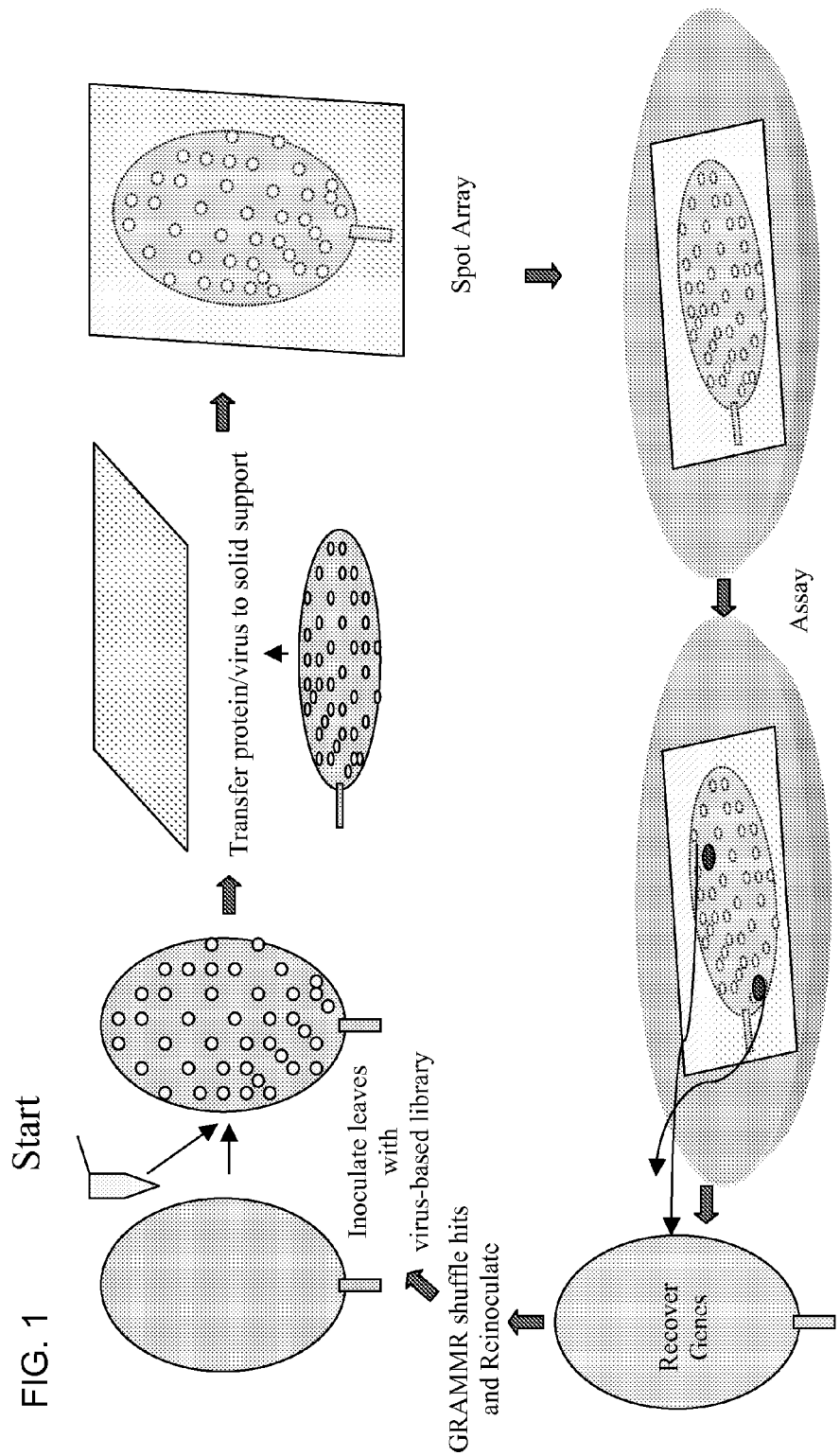
FIG. 1 diagrams an exemplary embodiment of the basic workflow of the invention.
Figure 2:
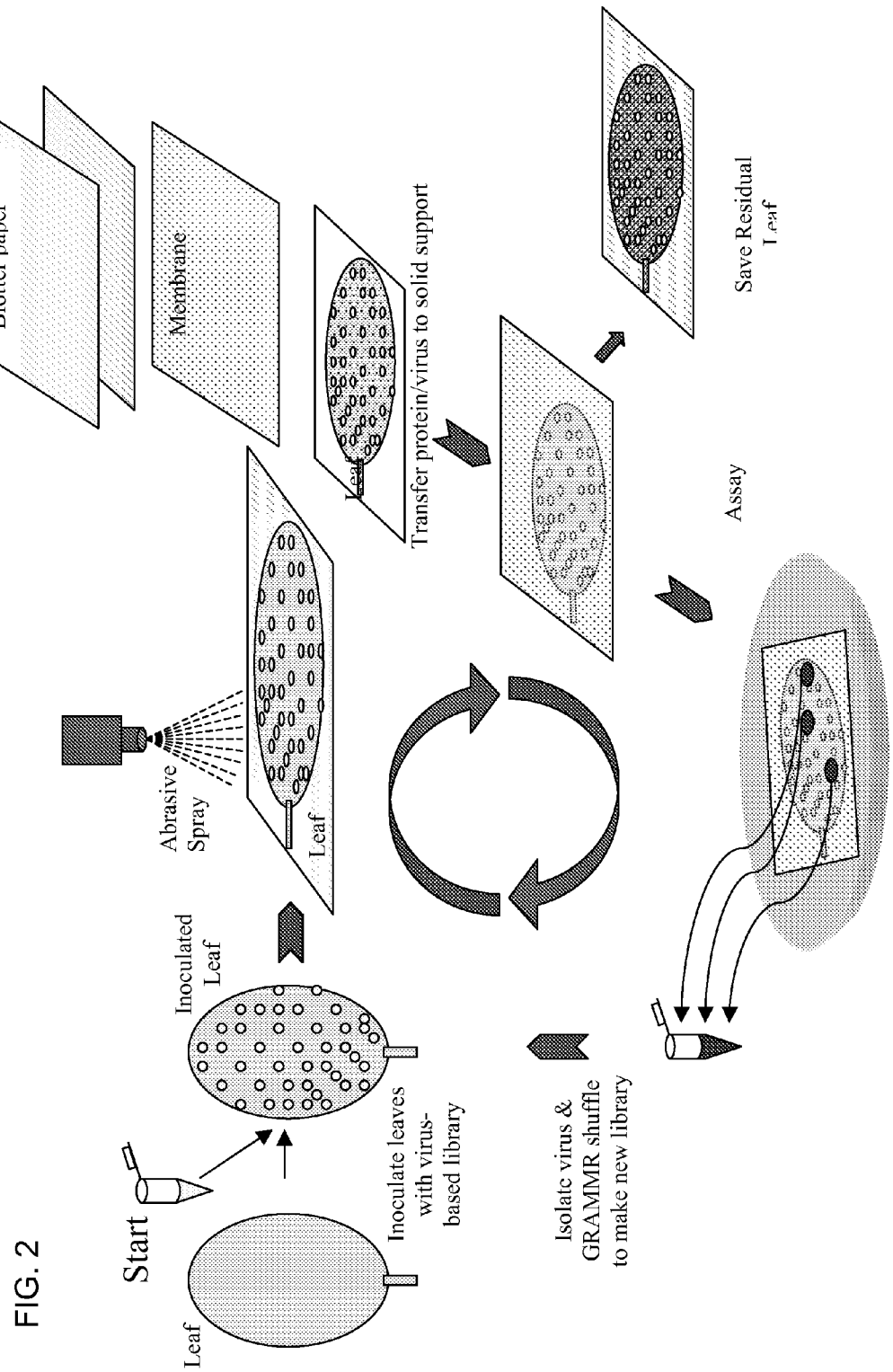
FIG. 2 diagrams an alternative exemplary embodiment of the basic workflow of the invention.
Figure 3:
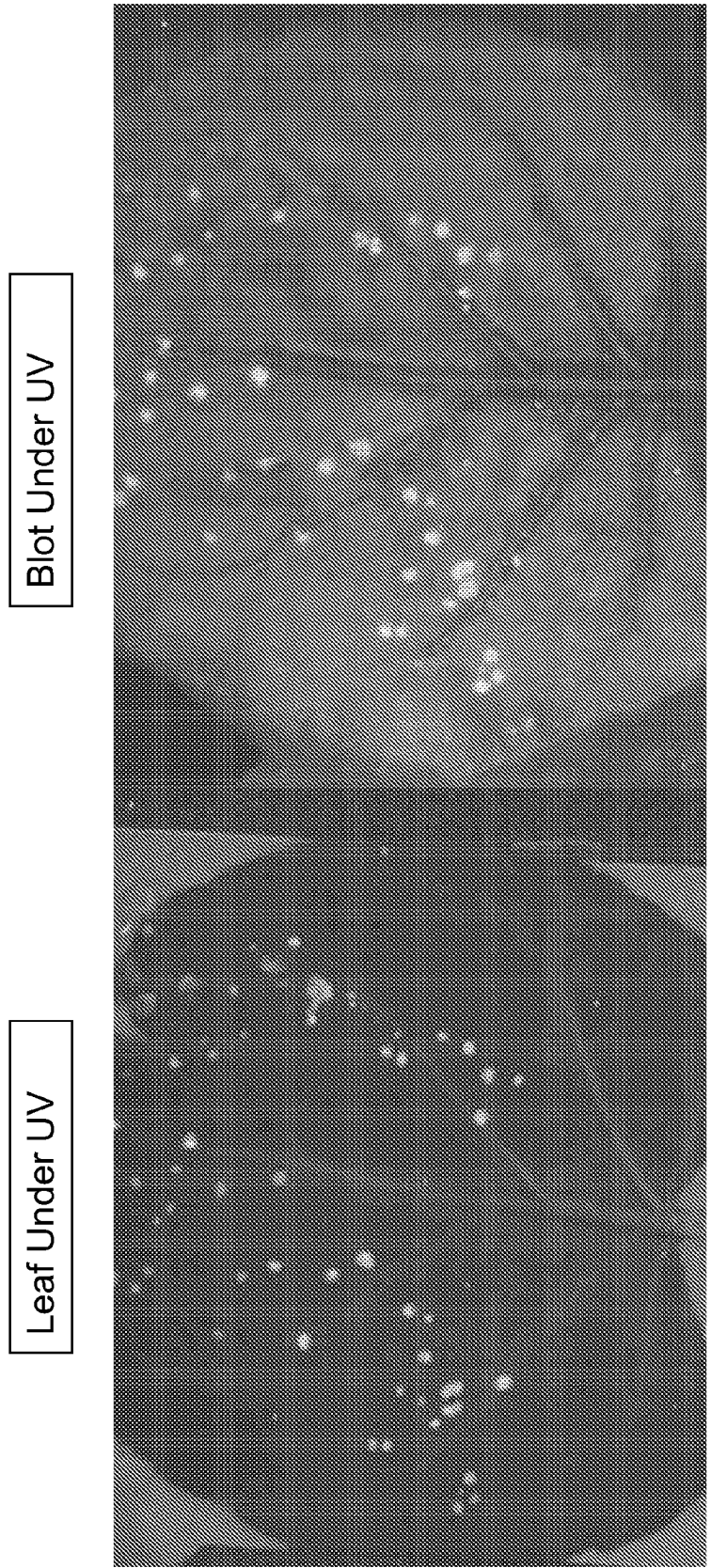
FIG. 3 depicts the results of an experiment in which a leaf of *N. benthamiana* was infected with a TMV-based viral vector containing the gene for GFP (green fluorescence protein) and then the infected leaf was blotted to a membrane. The left panel shows the infected leaf under UV illumination displaying infected foci with GFP fluorescence. The right panel shows the blot under UV illumination, and demonstrates fluorescent spots corresponding to those in the infected leaf.
Figure 4:
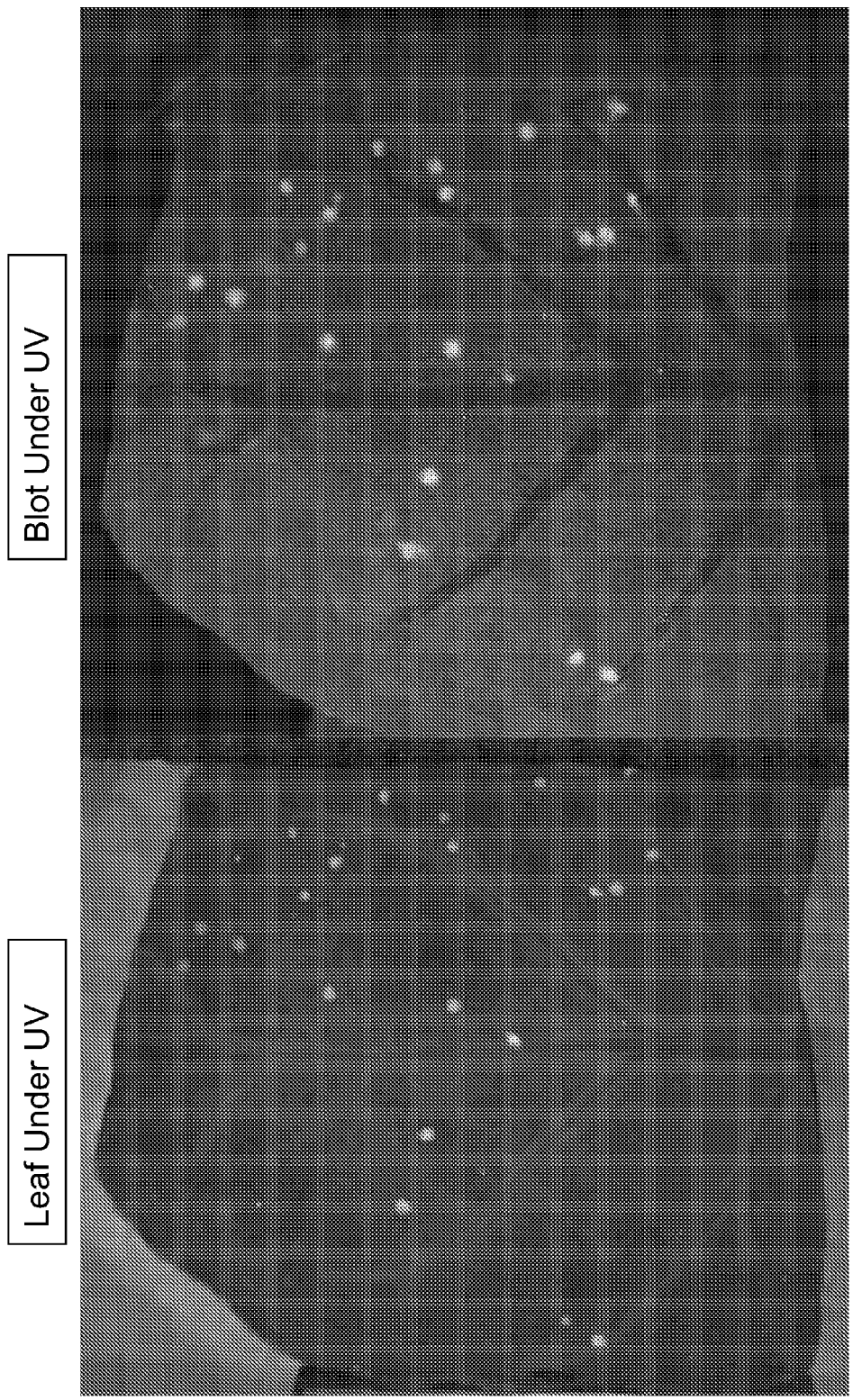
FIG. 4 depicts the results of the experiment described in FIG. 3 showing a different leaf.
Figure 5:
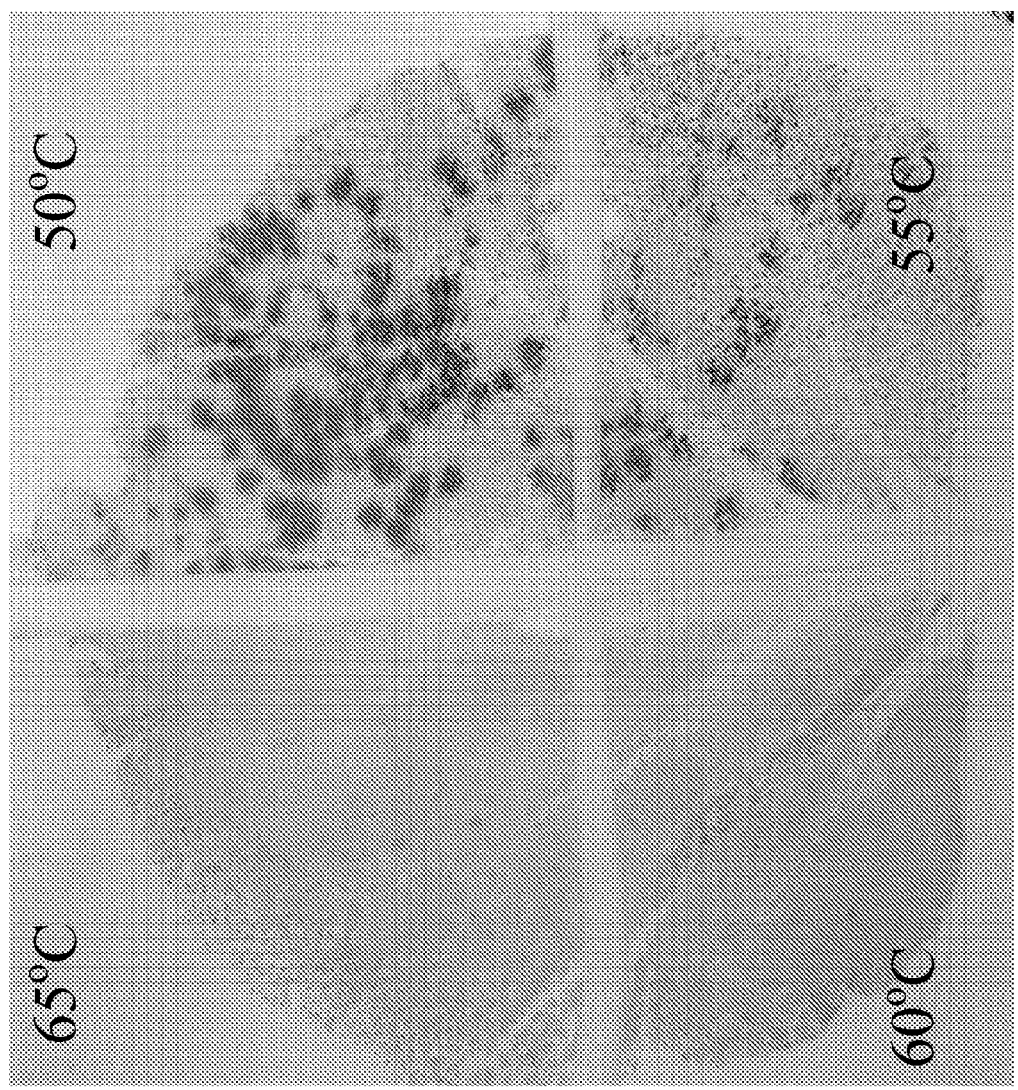
FIG. 5 depicts the results of an experiment in which a leaf of *N. benthamiana* was infected with a TMV-based viral vector containing the gene for beta-glucuronidase. The leaf was quartered and quarters were incubated with chromogenic substrate for beta-glucuronidase (GUS) at 50, 55, 60 or 65 degrees C.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention generally is a method for screening libraries of variant proteins produced in plant leaves using a plant viral vector to identify a gene of interest.

Here, we present a method of screening libraries of variant proteins produced in plant leaves using a plant viral vector. Each leaf infected with the viral vector library of variants can contain discrete foci of cells infected with the viral construct, each encoding an individual variant gene. First, the leaf can be pressed flat onto a backing, such as a sheet of adhesive film, and then lightly abraded before transferring the liquid contents of the leaf to a flexible solid support. The resulting blot, containing an impression of the leaf along with its contents, can then be subjected to an assay to detect the protein that was made in the virus-infected cells. Virus particles in the tissue can contain the nucleic acid encoding the protein. Since the virus can also adhere to the blot, spots containing a protein of interest can then be directly excised to recover virus. Alternatively, the leaf blot can be aligned to the residual leaf material followed by excision of both the spots and their corresponding leaf tissues.

Mounting the leaf on the adhesive backing can provide support to prevent tearing and disintegration of the leaf during the process of abrasion and transfer. The adhesive backing can also facilitate handling of the abraded leaf and provide a frame that can be given registration marks to track individual leaves and to precisely align the leaf blot to the leaf after transfer and assay have been performed. In an embodiment the adhesive backing can be of sufficient size for a leaf to be applied and of sufficient stickiness for the leaf to adhere and not detach during processing. Individual tape sheets used for covering 96-well format plates are convenient for this process, since they are roughly the correct size for a leaf from *Nicotiana benthamiana*, a typical host for plant virus expression vectors. They are available in a variety of adhesive coverings and polymer backings, and are also inexpensive and disposable.

Abrasion can disrupt the cuticle layer of the leaf and expose underlying cellular and extracellular contents of the leaf. In an embodiment a mode of abrading the leaf involves accelerating small particles in an air stream directed at the leaf. With sufficient particle speed and size, the surface of the leaf can be punctured, the cuticle and epidermal layer can be breached, and underlying cells can be wounded, thereby releasing their contents. The particles can be accelerated with a miniature-sandblasting device such as an artist airbrush that has been modified to pick up and deliver granular material in a stream of compressed air. In an embodiment an abrasive material can be crystalline sucrose, which is inexpensive, clean, nontoxic, nondenaturing, available in a range of particle sizes, and capable of penetrating the leaf tissues when accelerated to sufficient speed. After penetrating the leaf and disrupting cells, the sucrose crystals can dissolve, thereby reducing particulate residues that could interfere with transfer of the liquid material to the blot. The dissolving sucrose can also increase the viscosity of the cellular sap that has been released by wounding, in turn discouraging lateral diffusion and 'bleed-over' to adjacent areas of the abraded leaf. Finally, inert, water-soluble abrasives such as sucrose can later be washed away from the blot. Agents such as methylcellulose powder can also be added to the granular material to further increase viscosity. Additional agents can be added to prevent oxidation or other unwanted chemical reactions from occurring in the abraded leaf.

After mounting on an adhesive backing and abrading, the cellular contents can then be transferred to a membrane by appressing the mounted leaf to the membrane and allowing capillary action to transfer material. Because both virus and the recombinant protein it encodes bind to the membrane, this approach can maintain the spatial relationship between protein and gene in a two-dimensional blot.

The actual mode of transfer requires adequate contact between leaf and membrane to allow uniform transfer from leaf to blot. One way to do this can be to put the abraded side of the leaf against the membrane, place an absorbent blotter material on the other side of the membrane, and place the sandwiched leaf/membrane/blotter into a plastic vacuum sealer bag. Drawing a vacuum on the bag can gently press the leaf into the membrane, and excess liquid can be absorbed by the blotter behind the membrane to prevent unwanted lateral transfer of material (smearing) on the membrane. After the vacuum bag has been sealed, the leaf/membrane/blotter sandwich can be allowed to stand from a few seconds to many hours before opening the bag. Before separating the leaf/membrane assembly, registration marks can be made on the tape backing and membrane together to allow the two to be realigned after assay to facilitate recovery of additional material from the leaf if desired.

After recovery of virus from the excised blot and/or corresponding leaf tissue, the gene encoding the protein of interest can be isolated using standard molecular biology techniques. For RNA virus vectors such as ones based on the tobacco mosaic virus genome, the gene can be recovered by isolating virus from the blot and/or leaf, followed by extraction of the viral RNA and reverse transcription polymerase chain-reaction (rt-PCR). The gene can then be cloned back into the viral expression vector construct and shuffled with similar genes of interest followed by inoculation onto leaves for another round of screening. Alternatively, the amplified gene can be directly shuffled with similar genes, then ligated into the viral vector and transcribed to create inoculum for another round of screening.

In an alternative embodiment, the mounted and abraded leaf can be appressed to a semi-solid substrate such as agar or polyacrylamide and allowed to transfer material from the leaf into the gel.

In yet another embodiment, the abraded leaf can be overlaid with small beads that can adhere to virus particles as well as the recombinant proteins they encode. Each bead can land in a given area and adhere primarily to the virus particles and protein from that immediate area, thereby ensuring that the correspondence between a given gene and its encoded protein is maintained. The protein-covered beads can then be collected from the leaf surface, blocked to prevent unwanted binding, and then used for target binding or activity analysis. Beads that land on areas of leaf outside of virus infected areas can be expected to bind to only plant constituents and can simply represent background within the larger population of beads.

A major advantage of expressing libraries in leaves and screening using this leaf laminar blot approach can be that the proteins are produced in a eukaryotic host. The proteins can therefore be targeted to the endomembrane system for endoplasmic reticulum (ER) localization, secretion, folding, and a variety of post-translational modifications. Proteins can also be targeted to other cellular locations and organelles using the viral vector, and then be screened using the laminar blot approach. In effect, the leaves can be used as a uniform layer of cells in which distinct foci are infected with clonal populations of viruses expressing variant proteins. This system can provide a way to extract and assay many variant proteins simultaneously and then to recover the corresponding genes.

The virus library can be inoculated at a density of several hundred individual infection sites per leaf. At this inoculum density, infection foci of several millimeters across can be produced without overlap with one-another. Inoculation of a control virus expressing the green fluorescent protein can provide a visual cue to monitor infection site size. By inoculating several leaves per plant and using dozens, hundreds, or even thousands of plants, very large libraries of variants can be expressed and prepared for screening. The bead-based approach described above can provide even greater throughput. The cell-to-cell spread of a plant viral vector sometimes benefits from transgenic expression of viral genes, such as the viral movement protein, in the host plant. Use of such transgenic hosts can improve the cell-to-cell spread and consequent production of the variant proteins.

Exemplary steps in the process are outlined below.
Make Leaf Tissue Blots
Inoculate plant leaves (for example, *N. benthamiana*) with library of viruses expressing variant genes of interest
Several days post-inoculation, harvest leaf and stick one surface to tape pad sheet to immobilize leaf with other surface exposed
Abrade leaf with ultrafine sucrose (with methylcellulose to make sap more viscous) or other granular material using an artist airbrush fitted with a wide-bore venturi nozzle and an approximately 100 psi (pounds per square inch) airstream
Abrasion step requires care not to over- or under-abrade
Abraded areas should have darkened stippling without intervening light colored (un-abraded) areas
Leaf will weep slightly but liquid should not run or drip
Leaf Blotting:
Carefully lay tape with abraded leaf face down on nylon (or other) blot membrane (or gel slab)
Insert into vacuum seal bag with membrane backed by blotting paper
Vacuum seal to press leaf into membrane.
Leaf sap/cellular contents, etc transfer to blot and liquid pass through to blotting paper
Proteins, virus particles, and some debris, possibly organelles, including chloroplasts, stick to membrane Cut open bag after desired time interval Remove leaf/membrane/blotter sandwich, label and make registration marks on membrane and tape for future alignment.

Peel membrane from tape/leaf.

Wash membrane to remove any debris and residual sucrose

Set tape/leaf aside to dry

Membrane can be processed and used in a variety of assays, including;

1) Colorimetric, fluorometric, or other enzyme activity assay

2) Antibody blot

3) Protein-protein interaction blot

4) Degradation of toxic chemical in gel (agar) slab that then allows survival of overlaid cells.

5) Inhibition of growth of overlaid microorganisms

Recovery of Virus and Gene Cloning:

Excise spots from membrane and/or corresponding leaf tissue after matching up blot and leaf Extract virus from blot and/or leaf Extract nucleic acid from virus Isolate and clone gene of interest using standard molecular biology techniques It should be understood, of course, that the foregoing relates to exemplary embodiments of the invention and that modifications may be made without departing from the spirit and scope of the invention as set forth in the following claims.

What is claimed is:

1. A method of screening libraries of variant genes in plant leaves using a plant viral vector to identify a gene of interest, the method comprising:

a) inoculating plant leaves with a library of viruses expressing variant genes;

b) allowing sufficient time for a plurality of infected foci to form;

c) harvesting a leaf with infected foci, the leaf having two opposing faces;

d) sticking one face of the leaf to a sticky support material to immobilize the leaf and leaving the opposing face of the leaf exposed to form an exposed face;

e) abrading the exposed face of the leaf with granular material to form an abraded face;

f) appressing the abraded face to a semi-solid substrate and allowing transfer of material from the leaf into the semi-solid substrate;

g) removing the leaf from the semi-solid substrate;

h) performing an assay on the semi-solid substrate to identify an infected focus of interest;

i) recovering virus of interest corresponding to the infected focus of interest;

j) recovering nucleic acid from the virus of interest; and k) identifying the gene of interest from the nucleic acid.

2. The method of claim 1 wherein in step i) the virus of interest is recovered from the semi-solid substrate.

3. The method of claim 1 wherein in step i) the virus of interest is recovered from the leaf.

4. The method of claim 1 wherein the semi-solid substrate is agar or polyacrylamide.

5. A method of screening libraries of variant genes in plant leaves using a plant viral vector to identify a gene of interest, the method comprising:

a) inoculating plant leaves with a library of viruses expressing variant genes;

b) allowing sufficient time for a plurality of infected foci to form;

c) harvesting a leaf with infected foci, the leaf having two opposing faces;

d) sticking one face of the leaf to a sticky support material to immobilize the leaf and leaving the opposing face of the leaf exposed to form an exposed face;

e) abrading the exposed face of the leaf with granular material to form an abraded face;

f) appressing the abraded face to a semi-solid substrate and allowing transfer of material from the leaf into the semi-solid substrate;

g) removing the leaf from the semi-solid substrate; and h) performing an assay on the semi-solid substrate to identify an infected focus of interest.

\* \* \* \* \*